United States Patent [19]

Konishi et al.

[11] Patent Number: 4,992,376

[45] Date of Patent: Feb. 12, 1991

[54] **BIOLOGICAL PURE CULTURE OF *STREPTOMYCES VIOLACEUS* ATCC 53807**

[75] Inventors: Masataka Konishi, Kawasaki; Keiko Shimizu, Tokyo; Masaru Ohbayashi, Tokyo; Koji Tomita, Tokyo; Takeo Miyaki; Toshikazu Oki, both of Yokohama, all of Japan

[73] Assignee: Bristol-Myers Company, New York, N.Y.

[21] Appl. No.: 555,888

[22] Filed: Jul. 23, 1990

Related U.S. Application Data

[60] Continuation of Ser. No. 437,728, Nov. 17, 1989, which is a division of Ser. No. 246,393, Sep. 19, 1988, Pat. No. 4,927,848.

[51] Int. Cl.$^5$ ............................................. C12R 1/465
[52] U.S. Cl. .................................. 435/253.5; 435/886
[58] Field of Search ............................. 435/886, 253.5

[56] References Cited

U.S. PATENT DOCUMENTS

| | | | |
|---|---|---|---|
| 4,504,584 | 3/1985 | Kitaura et al. | 435/253.5 |
| 4,725,582 | 2/1988 | Kitaura et al. | 514/18 |
| 4,734,493 | 3/1988 | Yoshimoto et al. | 536/6.4 |
| 4,801,580 | 7/1989 | Kitaura et al. | 514/18 |
| 4,897,470 | 1/1990 | Yoshimoto et al. | 536/6.4 |

*Primary Examiner*—Herbert J. Lilling
*Attorney, Agent, or Firm*—David M. Morse

[57] ABSTRACT

An new antibiotic having the chromophore structure of the pluramycin family of antibiotics is produced by fermentation of *Streptomyces violaceus* ATCC 53807. The new antibiotic designated BU-3839T, exhibits potent antibacterial activity and also inhibits the growth of tumors in experimental animal systems.

1 Claim, No Drawings

BIOLOGICAL PURE CULTURE OF *STREPTOMYCES VIOLACEUS* ATCC 53807

This application is a divisional of co-pending application Ser. No. 437,728, filed Nov. 17, 1989 which is a divisional of application Ser. No. 246,393, filed Sept. 19, 1988, now U.S. Pat. No. 4,927,848.

BACKGROUND OF THE INVENTION

1. Field of the Invention

This invention relates to a novel antibiotic compound designated BU-3839T. BU-3839T exhibits antibacterial activity against gram-positive, gram-negative and anaerobic bacteria and also demonstrates both in vitro and in vivo antitumor activity.

2. Description of the Prior Art

Structural studies done on BU-3839T indicate that it contains the chromophore, 11-hydroxy-5-methyl-4H-anthra-[1,2-b]pyran-4,7,12-trione, found in the pluramycin family of antibiotics. Four antibiotics with this chromophore have been reported, α-indomycinone (*J. Antibiotics*, Ser A, 9, 75-81, 1956), SF-2330 (*J. Antibiotics* 39: 780-783, 1986), SS-43405D (Japan Kokai No. 61-139,394, June 26, 1986) and SS-43405E (Japan Kokai No. 61-189,280, Aug. 22, 1986). α-Indomycinone was reported to have no antimicrobial activity, while SF-2330 and SS-43405D were shown to have antibacterial activity. No antitumor activity has been reported for any of the above-mentioned antibiotics.

The structures of α-indomycinone, SF-2330, SS-43405D, SS-43405E, and BU-3839T are shown below. BU-3839T can be distinguished from the other antibiotics by the unique alkyl side chain ($R_1$) at the C-2 position of the chromophore.

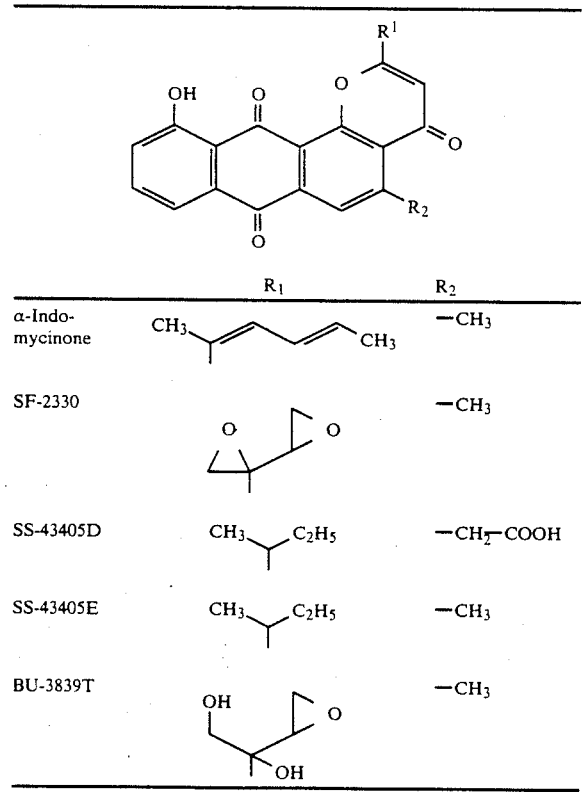

SUMMARY OF THE INVENTION

The present invention provides the antibiotic BU-3839T which exhibits activity against a variety of gram-positive, gram-negative and anaerobic bacteria. Additionally, BU-3839T exhibits in vitro and in vivo antitumor activity.

BU-3839T is obtained by cultivating a BU-3839T-producing strain of *Streptomyces violaceus* in an aqueous nutrient medium containing assimilable sources of carbon and nitrogen under submerged aerobic conditions until a substantial amount of BU-3839T is produced by said organism in said culture medium and then recovering the BU-3839T from said culture medium.

In another aspect there are provided pharmaceutical compositions useful for treating bacterial or carcinostatic infections in a mammalian host comprising an effective bacterial-inhibiting or tumor-inhibiting amount of BU-3839T together with a pharmaceutically acceptable carrier.

In a further aspect the present invention provides a method of treating bacterial infections in an animal host by administering to said host an effective antibacterial amount of BU-3839T, or a pharmaceutical composition thereof.

Finally the present invention provides a method of inhibiting the growth of tumors in a mammalian host by administering to said host a tumor-inhibiting amount of BU-3839T, or a pharmaceutical composition thereof.

DETAILED DESCRIPTION

The BU-3839T antibiotic of the present invention is produced by fermentation of a BU-3839T-producing strain of *Streptomyces violaceus*. The preferred producing organism is a novel strain of *Streptomyces violaceus* designated herein as *Streptomyces violaceus* strain P950-4. This strain was isolated from a soil sample collected in Hyderabad, Andhra Pradesh State, India. A biologically pure culture of strain P950-4 has been deposited with the American Type Culture Collection (ATCC), Washington, D.C. and added to its permanent collection of microorganisms as ATCC 53807.

Strain P950-4 has the following properties:

Morphology

Strain P950-4 forms both substrate and aerial mycelia, which are long, well-branched and not fragmented into short elements. Chains of spores are formed on the monopodially branched aerial hyphae. The spore chains are loop or compact spiral in shape, and contain 10 to 50 spores per chain. The spores are spherical to oval (0.6×0.6−0.9 μm) and have spiny surface. Motile spores and sporangium-like bodies are not observed.

Cultural Characteristics (Table 1)

The aerial mycelium are well formed on most agar media, but poorly on glucose-asparagine agar and not on ISP medium No. 6. The color of aerial mycelium is white, later turning to light grayish pink with sporulation. Melanin is produced distinctly in ISP medium No. 6, poorly in ISP No. 1, but not in ISP No. 7. A reddish-orange to purplish-red pigment, which is more or less diffusible, is formed in ISP media Nos. 2 and 7, Bennett's agar and Czapek's sucrose-nitrate agar. The pigment is pH-sensitive (yellowish-orange in acid and violet in alkali).

Physiological Characteristics (Table 2)

The growth is observed between 17° C. and 40° C., but not at 15° C. and 43° C. Tyrosinase reaction is positive. All of eleven diagnostic sugars are utilized for growth.

dylethanolamine and phosphotidylinositol, and therefore is placed in Type P-II.

Taxonomic Position

The morphology, cultural and physiological characteristics and cell chemistry reveal that Strain P950-4 is a

TABLE 1

Cultural characteristics of Strain P950-4

| Medium | Growth | Aerial mycelium | Substrate mycelium | Diffusible pigment |
|---|---|---|---|---|
| Sucrose-nitrate agar (Czapek-Dox agar) | Good | Moderate, white (263) | Light yellowish brown (76) to vivid dark purplish red (260) | Brownish orange (54) |
| Tryptone-yeast extract broth (ISP No. 1) | Moderate, not turbid | | Colorless | Deep brown (56) |
| Yeast extract-malt extract agar (ISP No. 2) | Good | Good; grayish yellowish pink (32) | Pale yellow (89) to brownish orange (54) | Strong yellowish brown (74) |
| Oat meal agar (ISP No. 3) | Moderate | Moderate; grayish pink (8) | Pale yellow (89) | None |
| Inorganic salts-starch agar (ISP No. 4) | Moderate | Moderate; grayish pink (8) | Deep yellow (85) | None |
| Glycerol-asparagine agar (ISP No. 5) | Moderate | Moderate; grayish pink (8) | Strong yellowish brown (74) | Moderate yellow (87) |
| Peptone-yeast extract-iron agar (ISP No. 6) | Moderate | None | Colorless | Brownish black (65) |
| Tyrosine agar (ISP No. 7) | Moderate | Moderate; yellowish white (92) | Light olive brown (94) | Dark grayish yellow (91) |
| Glucose-asparagine agar | Poor | Scant; white (263) | Pale yellow (89) | None |
| Nutrient agar | Poor | None | Colorless | Dark brown (59) |
| Bennett's agar | Good | Moderate; white (263) | Deep yellowish brown (75) | Moderate yellowish brown (77) |
| Papavizas' V-8 juice-dextrose-yeast extract agar | Moderate | Moderate; grayish yellowish pink (32) | Dark grayish reddish brown (47) | Deep brown (56) |

Observation after incubation at 28° C. for 3 weeks.
Color and number in parenthesis follow ISCC-NBS designation.

TABLE 2

Physiological characteristics of Strain P950-4

| Hydrolysis of: | | Utilization of** | |
|---|---|---|---|
| Gelatin | + | Glycerol | + |
| Starch | + | D-Arabinose | − |
| | | L-Arabinose | + |
| Milk coagulation | + | D-Xylose | + |
| peptonization | + | D-Ribose | + |
| | | L-Rhamnose | + |
| Production of: | | D-Glucose | + |
| | | D-Galactose | + |
| Nitrate reductase* | +/+ | D-Fructose | + |
| Tyrosinase | + | D-Mannose | + |
| | | L-Sorbose | − |
| Tolerance to: | | Sucrose | + |
| | | Lactose | + |
| Lysozyme 0.01% | ± | Cellobiose | + |
| 0.001% | ± | Melibiose | + |
| None | + | Trehalose | + |
| NaCl 1–7% | + | Raffinose | + |
| 8% | − | D-Melezitose | + |
| pH | 4.3~10.5 | Soluble starch | + |
| | | Cellulose | − |
| Temperature: | | Dulcitol | − |
| | | Inositol | + |
| Growth range | 17–40° C. | D-Mannitol | + |
| Optimal growth | 33–38° C. | D-Sorbitol | ± |
| No growth | 12° C. and 43° C. | Salicin | ± |

*Czapek's sucrose-nitrate broth/peptone-nitrate broth
**Basal medium: Pridham-Gottlieb's inorganic medium (ISP Medium No. 9)

Cell Chemistry

The whole cell hydrolysate contains LL-diaminopimelic acid, glucose and ribose, and hence the cell wall belongs to Type I and the sugar pattern NC. The phospholipid contains diphosphatidylglycerol, phosphatidylethanolamine and phosphotidylinositol, and therefore is placed in Type P-II.

species of Streptomyces. According to the descriptions of Pridham and Tresner[1], the major characteristics of Strain P950-4 are as follows: (A) color of sporulated aerial mycelium, red (R), (B) spore-chain morphology, Spira (S), (C) melanoid pigments, positive (C+), (D) spore wall ornamentation, echinulate (spiny). A species group with the above properties is shown in Table 17.44e (page 812), in which nine species and two subspecies are described.[1] These species and subspecies are fairly related to each other. According to the descriptions of Shirling and Gottlieb[2], Strain P950-4 is closely related to *Streptomyces violaceus* (Rossi Doria) Waksman 1953 in the medium specificity of melanoid formation, the pH-indicative property of a reddish pigment, and the sugar utilization pattern. Thus, Strain P950-4 was classified as *Streptomyces violaceus*.

[1] Pridham, T. G. and H. D. Tresner: Genus Streptomyces Waksman and Henrici, 1943, p. 748–829. In R. E. Buchanan and N. E. Gibbons (ed.), Bergey's Manual of Determinative Bacteriology, 8th ed. 1974. The Williams & Wilkins Co., Baltimore.
[2] Shirling, E. B. and D. Gottlieb: Cooperative description of type cultures of Streptomyces. II. Species descriptions. Int. J. Syst. Bacteriol. 18: 69–189, 1968; Ibid. 18: 279–392, 1968; Ibid. 19: 391–512, 1969; Ibid. 22: 265–394, 1972.

It is to be understood that the present invention is not limited to use of the particular preferred Strain P950-4 described above or to organisms fully answering the above descriptions. It is especially intended to include other BU-3839T-producing variant or mutant strains of the said organism which can be produced by conventional means such as x-radiation, ultraviolet radiation, treatment with nitrogen mustards, phage exposure, and the like.

Preparation of BU-3839T

BU-3839T is produced by cultivating a BU-3839T-producing strain of *Streptomyces violaceus*, most preferably a strain having the characteristics of *Streptomyces violaceus* strain P950-4 (ATCC 53807) or a variant or mutant thereof, under submerged aerobic conditions in an aqueous nutrient medium. The producing organism is grown in a nutrient medium containing an assimilable carbon source, for example L-arabinose, D-xylose, D-ribose, D-glucose, D-fructose, sucrose, lactose, cellobiose, D-mannitol or soluble starch. The nutrient medium should also contain an assimilable nitrogen source such as fish meal, peptone, soybean flour, peanut meal, cottonseed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate, or like ions.

Production of BU-3839T can be effected at any temperature conducive to satisfactory growth of the organism, e.g. 17°–40°, and is conveniently carried out at a temperature of about 28° C.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of BU-3839T. The medium in which the vegetative inoculum is produced can be the same as, or different from, that utilized in the tank as long as it is such that a good growth of the producing organism is obtained.

In general, optimum production of BU-3839T is achieved after incubation periods of about 2–3 days. Antibiotic production can be monitored by the paper disc-agar diffusion assay using *Bacillus subtilis* M45 (rec$^-$) as the test organism and in vitro cytotoxic activity against B16 melanoma cells.

Isolation and Purification

BU-3839T may be isolated from the fermentation broth by conventional isolation and purification procedures, i.e. solvent extraction and chromatography. Example 2 below illustrates a typical isolation and purification procedure for obtaining BU-3839T in substantially pure form.

Physicochemical Properties

BU-3839T was obtained as yellowish-orange needles which melted at 255° C. with decomposition. It was soluble in dimethyl sulfoxide and N,N-dimethylformamide, slightly soluble in chloroform, methylene chloride and alkaline water, and almost insoluble in other organic solvents and water. It gave a positive response to ferric chloride reagent, but gave no coloration with ninhydrin, anthrone and Sakaguchi tests. The physicochemical properties of BU-3839T are summarized below in Table 3. The molecular formula of the antibiotic was established as $C_{22}H_{16}O_8$ by the mass spectrum (M$^+$m/z:408) and microanalysis. BU-3839T exhibited UV absorption maxima at 240, 267, 286 (shoulder) and 417 nm in methanol and acidic methanol which shifted to 243, 282 (shoulder), 324 and 518 nm in alkaline solution. The IR spectrum showed characteristic absorptions at 1670, 1650, 1640, 1630 and 1580 cm$^{-1}$ suggesting a quinone moiety.

TABLE 3
Physicochemical Properties

| | | |
|---|---|---|
| Nature | Yellowish-orange needles | |
| M.P. | 255° C. (dec.) | |
| $[\alpha]_D^{25.0}$ | +26° ± 4 (c 0.25, DMF) | |
| UV $\lambda_{max}(\epsilon)$ | | |
| in MeOH | 240(36,900), 267(19,900), 286(sh), 417(6,800) | |
| in 0.1N HCl-MeOH | 240(32,200), 267(17,500), 286(sh), 417(6,200) | |
| in 0.1N NaOH-MeOH | 243(35,700), 282(sh), 324(8,000), 518(5,500) | |

| Analysis | Found | Calcd for $C_{22}H_{16}O_8$ |
|---|---|---|
| | C  64.86 | C  64.71 |
| | H  3.93 | H  3.95 |
| EI-MS (m/z) | 408 (M$^+$) | |
| TLC, SiO$_2$ | | |
| CH$_2$Cl$_2$-MeOH (9:1) | Rf 0.51 | |
| EtOAc-MeOH (4:1) | 0.63 | |

TABLE 4
$^1$H-NMR data of BU-3839T (400 MHz, in DMSO-d$_6$)

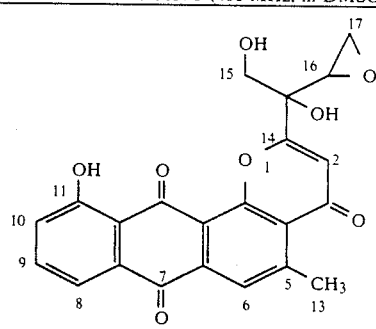

| Chemical shift δ (ppm) | Proton | Multiplicity (J = Hz) | Assignments |
|---|---|---|---|
| 2.72 | 1H | dd (4.0 and 5.6) | H-17 |
| 2.86 | 1H | dd (2.8 and 5.6) | H-17 |
| 2.91 | 3H | s | H-13 |
| 3.64 | 1H | dd (2.8 and 4.0) | H-16 |
| 3.82 | 1H | dd (6.1 and 11.3) | H-15 |
| 4.21 | 1H | dd (6.1 and 11.3) | H-15 |
| 5.02 | 1H | t (6.1) | C-15 OH |
| 5.72 | 1H | s | C-14 OH |
| 6.52 | 1H | s | H-3 |
| 7.42 | 1H | d (8.1) | H-10 |
| 7.72 | 1H | d (7.3) | H-8 |
| 7.79 | 1H | dd (7.3 and 8.1) | H-9 |
| 7.97 | 1H | s | H-6 |
| 12.64 | 1H | s | C-11 OH |

Structure Determination

The UV absorptions and observed pH shifts of BU-3839T suggested a close resemblance to those of the pluramycin group of antibiotics. The $^1$H-NMR spectrum revealed the presence of a total of 16 protons which were analyzed as 5 aromatic protons and 1 methyl, 2 methylene, 1 methine and 3 hydroxy groups. The presence of these functionalities was ascertained by the $^{13}$C-NMR spectrum. The spectrum exhibited 3 carbonyl (178.0, 181.2, 186.6 ppm), 14 sp$^2$ (with proton×5, 111.3, 118.6, 124.6×2, 136.5 ppm and without proton×9, 116.7, 119.7, 125.7, 132.0, 135.6, 148.2, 155.5, 161.3, 168.9 ppm) and 1 quaternary carbon (74.2 ppm) in addition to 1 methyl (23.1 ppm), 2 methylene (41.8, 65.1 ppm) and 1 methine carbon (53.2 ppm) signals. Unlike those of the common pluramycin group of antibiotics, the $^1H-$ and $^{13}C-$NMR spectra of BU-3839T did not show the signals assignable to amino or neutral sugar. The molecular formula assigned to the antibiotic ($C_{22}H_{16}O_8$) also showed the absence of an amino functionality in the molecule. The combined information, thus, suggested that BU-3839T had the chromophore structure of the pluramycin family of antibiotics. Three antibiotics with such type of structure, indomycinones, SF-2330 and SS-43405D and E have been reported. The $^1H-$ and $^{13}C-$NMR data described for SF-2330 were nearly identical with those of BU-3839T in the chromophore moiety and the differences appeared to reside only in the alkyl side chain of the 4-carbon unit ($^{13}C-$NMR: 41.8 t, 53.2 d, 65.1 t and 74.2 s). The behavior of UV maxima of BU-3839T and SF-2330 was consistent at different pHs. The $^1H$-NMR spectrum (in DMSO-d6) of the side chain moiety showed 7 protons, which were analyzed as two ABX's (2.72, 2.86 and 3.64 ppm and 3.82, 4.21 and 5.02 ppm), and an isolated hydroxyl proton (5.72 ppm). Upon $D_2O$ addition, the hydroxyl proton and one of the lower-field ABX proton (5.02 ppm) disappeared with concomitant collapsing of the ABX to a AB quartet. The spectroscopic results taken together with the earlier physico-chemical data indicated the following structure for BU-3839T.

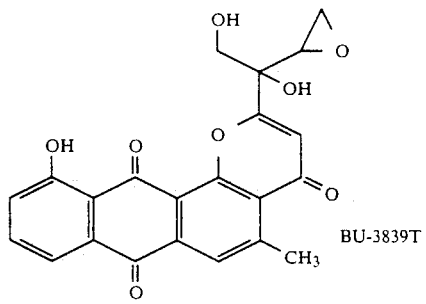

BU-3839T

Biological Activity

Antimicrobial Activity

Antimicrobial activity of BU-3839T was tested against a variety of bacteria and fungi by a two-fold serial dilution in agar media. As shown below in Table 5, BU-3839T exhibited remarkable inhibitory activity against gram-positive bacteria but relatively weak activity against gram-negative and anaerobic bacteria. Yeast and fungi were not susceptible to the antibiotic.

TABLE 5

| Antimicrobial activity | | | |
|---|---|---|---|
| Test organism | | Medium* | MIC (mcg/ml) |
| Staphylococcus aureus | 209P | NA | 0.05 |
| Staphylococcus aureus | Smith | NA | 0.05 |
| Staphylococcus aureus | A20234 | NA | 0.05 |
| Staphylococcus epidermidis | D153 | NA | 0.1 |
| Streptococcus faecalis | A9612 | NA | 0.4 |
| Streptococcus pyogenes | A20201 | NA | 0.1 |
| Micrococcus luteus | PCI 1001 | NA | 0.025 |
| Bacillus subtilis | PCI 219 | NA | 0.05 |
| Escherichia coli | NIHJ | NA | >50 |
| Klebsiella pneumoniae | D11 | NA | 6.3 |
| Pseudomonas aeruginosa | A9930 | NA | >50 |
| Proteus vulgaris | A9436 | NA | 6.3 |
| Proteus mirabilis | A9554 | NA | >50 |
| Bacteroides fragilis | A22035 | GAM | 0.1 |
| Clostridium difficile | A21675 | GAM | 0.4 |

TABLE 5-continued

| Antimicrobial activity | | | |
|---|---|---|---|
| Test organism | | Medium* | MIC (mcg/ml) |
| Clostridium perfringens | A9635 | GAM | 0.4 |
| Preopionibacterium acnes | A21933 | GAM | 0.8 |
| Candida albicans | IAM 4888 | SDA | >50 |
| Cryptococcus neoformans | D49 | SDA | >50 |
| Aspergillus fumigatus | IAM 2530 | SDA | >50 |
| Trichophyton mentagrophytes | D155 | SDA | >50 |

*NA: Nutrient agar
GAM: Gifu anaerobic medium agar
SDA: Sabouraud dextrose agar

Antitumor activity

BU-3839T was tested for in vitro cytotoxicity against murine and human tumor cells and for in vivo antitumor activity in mice. Mitomycin C was used as a reference compound in both in vitro and in vivo experiments. B16-F10 (murine melanoma) and Moser (human colorectal carcinoma) cells were grown to the logarithmic phase in the enriched Eagle minimum essential medium (MEM) supplemented with fetal calf serum (FCS, 10%) and kanamycin (60 mcg/ml), and HCT-116 (human colon carcinoma) cells were also grown to the logarithmic phase in Maccoy's 5A medium supplemented with FCS (10%), penicillin (100 $\mu$/ml) and streptomycin (100 mcg/ml). The tumor cells were harvested and implanted into wells of the 96-well microtiter plate with test materials at the inoculum sizes of $3.0 \times 10^4$, $6.0 \times 10^4$ and $6.0 \times 10^4$ cells/ml, respectively. They were incubated at 37° C. in humidified atmosphere of 5% $CO_2$ and 95% air for 72 hours. The cytotoxic activities against the above tumor cell lines were determined colorimetrically at 540 nm after staining viable cells with neutral red. The results were summarized in Table 6. Cytotoxicities of BU-3839T were quite potent against these tumor cells and were approximately 300-600 times superior to those of mitomycin C in terms of $IC_{50}$ value. Inhibitory effects of BU-3839T on macromolecule (DNA, RNA and protein) synthesis were determined in vitro. Cultured L1210 murine leukemia cells ($5 \times 10^5$ cells/ml) were incubated with test materials at 37° C. for 15 min. Labelled precursor, $^3H$-thymidine, $^{14}C$-uridine or $^3H$-leucine was added into the cultured mixtures and further incubated for 60 min. After washing with chilled 5% trichloroacetic acid solution, the radioactivity incorporated into the acid-insoluble fraction of the tumor cells was determined in a liquid scintillation counter. As shown in Table 7, in contrast to mitomycin C which showed specific inhibition of DNA synthesis, BU-3839T inhibited DNA, RNA and protein synthesis non-specifically. In vivo antitumor activity of BU-3839T was tested in the experimental mouse tumor systems. Female $CDF_1$ and male $BDF_1$ mice were intraperitoneally inoculated with 0.4 ml of diluted ascitic fluid containing $10^6$ lymphocytic leukemia P388 cells and 0.5 ml of 10% melanotic melanoma B16 brei, respectively. Test compounds were administered intraperitoneally by the following dosing schedules; once a day on days 1, 2 and 3 ($QD \times 3$) or on days 1, 5 and 9 ($Q4D \times 3$). As shown in Tables 8 and 9, BU-3839T demonstrated relatively broad and moderate chemotherapeutic activity against P388 leukemia with maximum T/C value of 145%, whereas it showed minimum antitumor activity against ip-B16 melanoma at the doses tested.

TABLE 6

In vitro cytotoxicities against murine and human tumor cells

| | IC$_{50}$ (mcg/ml) | | |
|---|---|---|---|
| Compound | B16-F10 | Moser | HCT-116 |
| BU-3839T | 0.0009 | 0.0046 | 0.0026 |
| Mitomycin C | 0.50 | 1.2 | 0.80 |

TABLE 7

Inhibition of macromolecule synthesis in L1210 leukemia cells

| | IC$_{50}$ (mcg/ml) | | |
|---|---|---|---|
| Compound | DNA | RNA | Protein |
| BU-3839T | 0.013 | 0.029 | 0.039 |
| Mitomycin C | 1.7 | >100 | >100 |

TABLE 8

Antitumor activity against P388 leukemia (ip)

| Compound | Dose*[1] (mg/kg/day) | MST*[2] (day) | T/C (%) | Body weight change on day 4 (g) |
|---|---|---|---|---|
| BU-3839 T | 1.0 | 7.0 | 70 | −2.5 |
| | 0.5 | 14.5 | 145*[3] | −2.3 |
| | 0.25 | 12.5 | 125*[3] | −1.8 |
| | 0.13 | 14.0 | 140*[3] | −0.5 |
| | 0.063 | 13.0 | 130*[3] | +0.8 |
| | 0.031 | 12.5 | 125*[3] | +1.3 |
| | 0.016 | 11.5 | 115 | +1.0 |
| | 0.008 | 11.0 | 110 | +1.0 |
| Mitomycin C | 2 | 20.0 | 200*[3] | −1.8 |
| | 1 | 14.5 | 145*[3] | −0.3 |
| | 0.5 | 15.0 | 150*[3] | −0.5 |
| | 0.25 | 13.0 | 130*[3] | +1.5 |
| Vehicle | — | 10.0 | — | +1.4 |

*[1]QD × 3, ip
*[2]Median survival time
*[3]Significant antitumor effect (T/C ≧ 125%)

TABLE 9

Antitumor activity against B16 melanoma (ip)

| Compound | Dose*[1] (mg/kg/day) | MST*[2] (day) | T/C (%) | Body weight change on day 5 (g) |
|---|---|---|---|---|
| BU-3839 T | 2.0 | Tox | Tox | — |
| | 1.0 | 10.0 | 74 | −3.3 |
| | 0.5 | 11.0 | 81 | −3.8 |
| | 0.25 | 17.0 | 126*[3] | −0.5 |
| | 0.13 | 15.5 | 115 | +0.5 |
| | 0.063 | 16.5 | 122 | +0.8 |
| Mitomycin C | 2.0 | 30.0 | 222*[3] | +0.5 |
| | 1.0 | 20.5 | 152*[3] | +1.0 |
| | 0.5 | 18.0 | 133*[3] | 0.0 |
| | 0.25 | 15.0 | 111 | +0.8 |
| Vehicle | — | 13.5 | — | +1.0 |

*[1]Q4D × 3, ip
*[2]Median survival time
*[3]Significant antitumor effect (T/C ≧ 125%)

As shown above BU-3839T possesses potent antibacterial activity and is thus useful in the therapeutic treatment of mammals and other animals for diseases caused by such organisms. Additionally, the compound may be utilized for other conventional in vitro applications of antibacterial agents such as disinfecting medical and dental equipment.

The in vitro and in vivo antitumor data presented above indicate that BU-3839T is also therapeutically useful in inhibiting the growth of malignant tumors in mammalian hosts.

The present invention, therefore, provides a method for therapeutically treating an animal host affected by a bacterial infection, which comprises administering to said host an effective antibacterial dose of BU-3839T, or a pharmaceutical composition thereof.

Also provided is a method for inhibiting the growth of malignant tumors in mammals which comprises administering to said mammalian host an effective tumor-inhibiting dose of BU-3839T, or a pharmaceutical composition thereof.

In another aspect the present invention provides a pharmaceutical composition which comprises an effective antibacterial amount of BU-3839T in combination with an inert pharmaceutically acceptable carrier or diluent.

Additionally, the invention provides a pharmaceutical composition which comprises an effective tumor-inhibiting amount of BU-3839T in combination with an inert pharmaceutically acceptable carrier or diluent.

The pharmaceutical compositions may contain other active antibacterial or antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparation for parenteral administration such as sterile solutions, suspensions or emulsions. They may also be manufactured in the form of sterile solid compositions which can be dissolved in sterile water, physiological saline or some other suitable sterile injectable medium immediately before use.

For use as an antimicrobial agent, the BU-3839T or pharmaceutical composition thereof, is administered so that the concentration of active ingredient is greater than the minimum inhibitory concentration for the particular organism being treated. For use as an antitumor agent, optimal dosages and regiments of BU-3839T for a given mammalian host can be readily ascertained by those skilled in the art. It will, of course, be appreciated that the actual dose of compound used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are provided for illustrative purposes only and are not intended to limit the scope of the invention. Unless otherwise indicated all volume ratios indicated below are volume/volume.

EXAMPLE 1

Fermentation of BU-3839T

A loopful of the slant culture of *Steptomyces violaceus* strain No. P950-4 was inoculated into a 500-ml Erlenmeyer flask containing 100 ml of the seed medium consisting of 2% glucose, 1% Pharmamedia (Traders) and 0.5% CaCO$_3$, the pH being adjusted to 7.0 before autoclaving. The fermentation was carried out at 28° C. for 4 days on a rotary shaker (200 rpm) and 5 ml of broth was transferred into a 500-ml Erlenmeyer flask containing 100 ml of production medium having the same composition as the seed medium. The fermentation was carried out for 3 days under the same conditions as the seed culture. The antitumor activity in fermentation broths was determined by the paper disc agar diffusion assay using *Bacillus subtilis* M45 (rec⁻) as the test organism and in vitro cytotoxic activity against B16 melanoma cells. The antibiotic potency of 7 μg/ml was obtained after three days cultivation.

The fermentation was also carried out in a jar fermentor. A 500 ml portion of the seed culture obtained by the flask fermentation was transferred into a 20 liter jar fermentor (Marubishi, MSJ-20) containing 12 liters of production medium having the same composition as the flask fermentation. The fermentation was run at 28° C. with agitation at 250 rpm and aeration rate of 12 liters per minute. The antibiotic production reached a maximum of 12 μg/ml after 40-50 hrs fermentation.

EXAMPLE 2

Isolation and Purification of BU-3839T

The whole harvested broth (50 L, pH 8.4) as produced in Example 1 was extracted with n-butanol (25 L) under vigorous stirring. The separated n-butanol phase was evaporated under reduced pressure to an aqueous solution (1 L) which was extracted three times with 1 L each of ethyl acetate. The organic extracts were combined and concentrated in vacuo to 200 ml of the solution. The solution was added dropwise to 2.3 L of n-hexane under stirring. The precipitates deposited were collected by filtration and dried in vacuo to yield the crude solid of BU-3839T (6.9 g).

The crude solid was dissolved in methylene chloride (50 ml) and applied on a column of silica gel ($\phi 5.0 \times 50$ cm) which had been pre-washed with methylene chloride. The elution was carried out with methylene chloride and an increasing amount of methanol (99.5:0.5-98:2). The eluate was checked by the bioassay using *Bacillus subtilis* M45 (rec⁻ mutant) and the active fractions eluted with methylene chloride-methanol (99:1-98:2) were pooled and concentrated in vacuo. Upon standing in a cold room, the concentrate deposited yellowish-orange needles of pure BU-3839T (109 mg). Rechromatography of the mother liquor and the subsequent active eluate afforded a further amount of pure BU-3839T (120 mg).

We claim:

1. A biologically pure culture of the microorganism *Streptomyces violaceus* ATCC 53807, which is capable of producing the antibiotic BU-3839T in a recoverable quantity upon cultivation in a culture medium containing assimilable sources of carbon and nitrogen under submerged aerobic conditions.

* * * * *